United States Patent [19]
Kamb

[11] Patent Number: 5,869,242
[45] Date of Patent: Feb. 9, 1999

[54] MASS SPECTROMETRY TO ASSESS DNA SEQUENCE POLYMORPHISMS

[75] Inventor: Alexander Kamb, Salt Lake City, Utah

[73] Assignee: Myriad Genetics, Inc., Salt Lake City, Utah

[21] Appl. No.: 529,879

[22] Filed: Sep. 18, 1995

[51] Int. Cl.$^6$ .............................. C12Q 1/68; G01N 24/00; B01D 59/44
[52] U.S. Cl. .......................... 435/6; 435/91.53; 436/173
[58] Field of Search .......................... 435/6, 91.2, 91.21, 435/91.53, 172.3, 320.1; 436/94, 173, 174; 935/76, 77; 250/282

[56] References Cited

U.S. PATENT DOCUMENTS

| | | | |
|---|---|---|---|
| 4,701,419 | 10/1987 | Morris | 436/89 |
| 5,003,059 | 3/1991 | Brennan | 536/25.32 |
| 5,064,754 | 11/1991 | Mills | 435/6 |
| 5,221,518 | 6/1993 | Mills | 422/62 |
| 5,424,184 | 6/1995 | Santamaria et al. | 435/6 |

OTHER PUBLICATIONS

Hillenkamp, F. et al. (1991). "Matrix–Assisted Laser Desorption/Ionization Mass Spectrometry of Biopolymers," *Anal. Chem.* 63:1193A–1203A.

Kirpekar, F. et al. (1994). "Matrix assisted laser desorption/ionization mass spectrometry of enzymatically synthesized RNA up to 150 kDa," *Nucl. Acids Res.* 22:3866–3870.

Nelson, R.W. et al. (1989). "Volatilization of High Molecular Weight DNA by Pulsed Laser Ablation of Frozen Aqueous Solutions," *Science* 246:1585–1587.

Nordhoff, E. et al. (1993). "Ion stability of nucleic acids in infrared matrix–assisted laser desorption/ionization mass spectrometry," *Nucl. Acids Res.* 21:3347–3357.

Nordhoff, E. et al. (1994). "Comparison of IR– and UV–matrix–assisted laser desorption/ionization mass spectrometry of oligodeoxynucleotides," *Nucl. Acids Res.* 22:2460–2465.

Pieles, U. et al. (1993). "Matrix–assisted laser desorption ionization time–of–flight mass spectrometry: a powerful tool for the mass and sequence analysis of natural and modified oligonucleotides," *Nucl. Acids Res.* 21:3191–3196.

Schneider, K. and Chait, B.T. (1995). "Increased stability of nucleic acids containing 7–deaza–guanosine and 7–deaza–adenosine may enable rapid DNA sequencing by matrix–assisted laser desorption mass spectrometry," *Nucl. Acids Res.* 23:1570–1575.

Siuzdak, G. (1994). "The emergence of mass spectrometry in biochemical research," *Proc. Natl. Acad. Sci. USA* 91:11290–11297.

Wang, B.H. and Biemann (1994). "Matrix–Assisted Laser Desorption/Ionization Time–of–Flight Mass Spectrometry of Chemically Modified Oligonucleotides," *Anal. Chem.* 66:1918–1924.

Wu, K.J. et al. (1994). "time–of–Flight Mass Spectrometry of Underivatized Single–Stranded DNA Oligomers by Matrix–Assisted Laser Desorption," *Anal. Chem.* 66:1637–1645.

*Primary Examiner*—George C. Elliott
*Assistant Examiner*—Thomas G. Larson
*Attorney, Agent, or Firm*—Rothwell, Figg, Ernst & Kurz, P.C.

[57] ABSTRACT

A method for determining the presence of polymorphisms, including mutations, in nucleic acids by using mass spectrometry is presented. The method requires amplification of the nucleic acid region to be analyzed followed by analysis by mass spectrometry and comparison of the obtained spectrum with spectra obtained from wild-type sequences and/or sequences known to contain the polymorphism. Differences between the spectra, either the appearance or disappearance of one or more peaks indicating a change in mass or a change in the height of one or more peaks indicating a change in the amount of nucleic acid of a specific mass, indicate the presence of a polymorphism. Variations of the method involve digestion of the amplified nucleic acid, e.g., by using restriction enzymes, nucleases or chemical methods, prior to analysis by mass spectrometry. The method can be applied to any type of nucleic acid including genomic DNA, CDNA and RNA. The method is especially well suited for performing routine genetic screening on a large scale for mutations known to be associated with a disease. The method is also appropriate for determining the presence of polymorphisms for other purposes, e.g., for genotyping or screening for mutations in a positional cloning project. A preferred approach is to amplify then digest the nucleic acid and then to analyze it via matrix-assisted laser desorption/ionization mass spectrometry (MALDI-MS) using a neodymium-garnet laser and a 3-hydroxypicolinic acid matrix.

12 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
      ( A ) LENGTH: 39 base pairs
      ( B ) TYPE: nucleic acid
      ( C ) STRANDEDNESS: double (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:1:

CAAAGCGAGC AAGAGAATCC CAGGACAGAA AGATCTTCA                    39

(2) INFORMATION FOR SEQ ID NO:2:

(i) SEQUENCE CHARACTERISTICS:
            (A) LENGTH: 40 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:2:

CAAAGCGAGC AAGAGAATCC CCAGGACAGA AAGATCTTCA                   40

(2) INFORMATION FOR SEQ ID NO:3:

(i) SEQUENCE CHARACTERISTICS:
            (A) LENGTH: 40 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:3:

TGGAGGAGCA ACAGCTGGAA GAGTCTGGGC CACACGATTT                   40

MASS SPECTROMETRY TO ASSESS DNA SEQUENCE POLYMORPHISMS

BACKGROUND OF THE INVENTION

The determination of the presence of polymorphisms, especially mutations, in DNA has become a very important and useful tool for a variety of purposes. Detecting mutations which are known to cause or to predispose persons to disease is one of the more important uses of determining the possible presence of a mutation. One example is the analysis of the gene named BRCA1 which may result in breast cancer if it is mutated (Miki et al., 1994; Futreal et al., 1994). Several known mutations in the BRCA1 gene have been causally linked with breast cancer. With this knowledge in hand it is now possible to screen women for these known mutations to determine whether they are predisposed to develop breast cancer. Some other uses for determining polymorphisms or mutations are for genotyping and for mutational analysis for positional cloning experiments.

A few different methods are commonly used to analyze DNA for polymorphisms or mutations. The most definitive method is to sequence the DNA to determine the actual base sequence (Maxam and Gilbert, 1977; Sanger et al., 1977). Although such a method is the most definitive it is also the most expensive and time consuming method. Restriction mapping analysis has some limited use in analyzing DNA for polymorphisms. If one is looking for a known polymorphism at a site which will change the recognition site for a restriction enzyme it is possible simply to digest DNA with this restriction enzyme and analyze the fragments on a gel or with a Southern blot to determine the presence or absence of the polymorphism. This type of analysis is also useful for determining the presence or absence of gross insertions or deletions. Hybridization with allele specific oligonucleotides is yet another method for determining the presence of known polymorphisms. These latter methods require the use of hybridization techniques which are time consuming and costly.

In recent years some breakthroughs have been made which allow the use of mass spectrometry to analyze macromolecules (Hillenkamp et al., 1991; Schneider and Chait, 1995; Wang and Biemann, 1994; Nordhoff et al., 1993; Siuzdak, 1994; Wu et al., 1994; Nelson et al., 1989; Nordhoff et al., 1994; Kirpekar et al., 1994; and Pieles et al., 1993). Many papers have now been published which establish that mass spectrometry can be used to analyze DNA fragments. Some papers have focused simply on the ability to measure the mass of a single fragment of DNA or RNA whereas others have gone so far as to show the utility of mass spectrometry for sequencing short fragments of nucleic acids (Pieles et al., 1993; Kirpekar et al., 1994). In all of the papers published to date the analysis has been limited to polynucleotides on the order of about 50 nucleotides or fewer. The appeal of mass spectrometry is the tremendous speed in obtaining data. Once samples have been prepared the throughput can be as fast as 1–2 seconds per sample. Analysis of the data is then done off-line. This time of 1–2 seconds is a tremendous advantage when compared with the many hours needed for running gels and/or hybridizing samples for analysis if the more classical methods of nucleic acid polymorphism analysis are used.

The present invention applies mass spectrometry to the determination of the presence of polymorphisms within known genes. The method uses mass spectrometry to compare the mass spectrum of a fragment of DNA from a sample to be analyzed with known reference mass spectra of DNA, e.g., spectra for wild-type DNA and DNA with a known polymorphism. Determination of the presence of a polymorphism in the sample being tested is rapid and accurate. The use of mass spectrometry with its very rapid analysis is especially useful for routine screening of large numbers of samples.

The publications and other materials used herein to illuminate the background of the invention, and in particular, cases to provide additional details respecting the practice, are incorporated herein by reference, and for convenience, are referenced by author and date in the text and respectively grouped in the appended List of References.

SUMMARY OF THE INVENTION

The invention is directed to determining the presence of polymorphisms in nucleic acids by analyzing the nucleic acid using mass spectrometry. Many different reasons exist for wanting to determine the presence of polymorphisms. One popular reason for doing this analysis is to determine if a person's genome contains a mutation known to be associated with a disease, e.g., cancer or heart disease. Such mutations are known and by analyzing for their presence, persons found to have such mutations can take preemptive action to treat or cure the disease associated with the mutation. A typical analysis involves sequencing the genes of interest. As more gene mutations associated with various diseases are discovered it is certain that more genetic analyses will be performed. The time and cost of present sequencing methods will limit the amount of genetic testing which can be done because DNA sequencing as done presently requires trained technicians and many hours of preparation and analysis. Newer methods which are faster and less costly to perform are necessary to allow for routine screening of mutations known to be associated with disease. As more disease causing mutations are found this need will become even more critical.

The present invention uses mass spectrometry rather than requiring the use of gels and/or nucleic acid hybridization techniques to analyze for polymorphisms. Once a sample has been prepared, data acquisition via mass spectrometry requires only a few seconds. This removes the hours of time required for techniques which require use of gel electrophoresis or nucleic acid hybridization. Time for sample preparation is still required just as for analysis by the established methods, but the analysis of the samples once prepared is tremendously faster using mass spectrometry.

One method of using the present invention is to prepare amplified DNA from a patient's sample in the region of a known mutation. The amplified DNA is then analyzed in a mass spectrometer to determine the mass of the amplified fragment.

The mass spectrum obtained is compared to the mass spectrum of fragments obtained from known samples of either wild-type genes or genes containing the known mutation. These known spectra are referred to as "signature" spectra. A simple comparison of the sample spectrum vs. signature spectra will reveal whether the patient's DNA contains a mutation. Although sequencing of fragments of nucleic acids is possible using mass spectrometry, actual sequencing of the nucleic acid is not required for this mutational analysis. Less preparation and analysis is needed to prepare and analyze a complete, intact fragment as compared to treating a sample for actual sequencing.

A variation of the above technique may also be used to analyze for polymorphisms. In this variation the fragments of nucleic acid are digested via any one of several techniques to smaller fragments which may range from one base up to approximately 50 bases. The resulting mix of fragments is then analyzed via mass spectrometry. The resulting spectrum contains several peaks and is compared with signature spectra of samples known to be wild-type or to contain a known polymorphism. A comparison of the locations (mass) and heights (relative amounts) of peaks in the sample with the known signature spectra indicate what type of polymorphism, if any, is present.

DESCRIPTION OF THE INVENTION

The invention is directed to a rapid method for analyzing for the presence of polymorphisms in a nucleic acid sample. The method utilizes mass spectrometry to analyze the nucleic acid. This method is much more rapid than other nucleic acid analysis techniques, e.g., DNA sequencing using polyacrylamide gel electrophoresis or hybridization techniques such as using allele specific oligonucleotides. A rapid technique is very desirable for routine screening of many samples. As more and more genes are identified, purified and sequenced, and determined to be associated with disease states when mutated, the number of requests for mutational analysis will grow. The present method, by greatly increasing the rate of analysis, will help meet the need for the vast amount of genetic testing expected in the near future.

One aspect of the present invention is the realization that it is unnecessary to analyze a complete gene for genetic or hereditary testing. Often it is found that only one or a few specific mutations are the cause of a disease in most, if not all, cases of the disease. For routine genetic screening for the disease it is necessary to analyze only the regions of nucleic acid in the immediate region of the known mutation. Knowledge of the nucleic acid composition in these relatively short regions will enable one to determine if the patient contains a harmful mutation. There is no need to analyze fully the complete gene sequence of a gene associated with a disease. It is another aspect of this invention that it is also now realized that one need not do an actual sequence analysis of even these short regions of nucleic acid to determine the presence of a polymorphism. Rather one can use a method which is exquisitely precise in determining the total composition of the fragments of DNA. Mass spectrometry is one such method which yields very precise results and is applicable to short nucleotide fragments. This invention teaches that a simple comparison of a mass spectrum of a total nucleic acid sample fragment with spectra of known fragments quickly yields data capable of determining the presence of a polymorphism in the sample. Alternatively, one can digest the fragment to yield a spectrum of several peaks, rather than a single peak representing the whole fragment, and use this spectrum to determine whether a polymorphism is present in the sample. This is again simpler and faster than sequencing the sample.

The disclosed methods are useful for determining the presence of a polymorphism in a nucleic acid sample for any purpose, it is not limited to testing for mutations in genes associated with a disease.

EXAMPLE I

Amplification of Nucleic Acid to be Analyzed

Relatively pure nucleic acid fragments must be obtained in sufficient amounts to be detectable by mass spectrometry. Matrix-assisted laser desorption/ionization mass spectrometry (MALDI-MS) is currently sensitive at the femtomole level (Siuzdak, 1994). Typically picomole amounts of nucleic acids are used in MALDI-MS analyses. A wide variety of techniques for preparing large amounts of purified fragments of nucleic acids are known to those of skill in the art. Several amplification techniques are commonly used. Polymerase chain reaction (PCR) is one very powerful technique for amplifying specific fragments of nucleic acids and is especially appropriate for the present invention. PCR requires knowledge of two small portions of about 15 bases or more each of the DNA sequence. Two primers are made, one corresponding to each known region, and these primers are designed such they will each prime synthesis of a different strand of DNA such that synthesis will be in the direction of one primer towards the other primer. The primers, DNA to be amplified, a thermostable DNA polymerase, a mix of the four deoxynucleotides, and a buffer are combined. DNA synthesis will occur. The solution is then denatured by heating, then it is cooled to allow annealing of new primer and another round of DNA synthesis occurs. This process is typically repeated for about 30 cycles resulting in an amplification of several million fold of the region of DNA internal to the two primers (including the region of the two primers). Many variations of PCR are known. One can begin with RNA, reverse transcribe the RNA to synthesize cDNA, and use the cDNA for the amplification template rather than using genomic DNA. Another alternative is to synthesize RNA rather than DNA to be analyzed via mass spectrometry. One method for preparing large quantities of RNA is to clone a fragment of DNA into a vector which has promoters specific for an RNA polymerase, e.g., a T7 or SP6 RNA polymerase promoter. These vectors can be linearized and RNA transcripts can be synthesized yielding a large quantity of homogeneous RNA. This amplified RNA can be used for the mass spectrometry analysis.

In synthesizing these amplified nucleic acids, one can incorporate a variety of nucleotide analogs into the nucleic acid if desired. One useful substitution is to incorporate deoxyuridine into amplified DNA. This is useful for producing small fragments by later digesting the amplified DNA with uracil-N-glycosidase. One other example of a useful substitution is to incorporate 7-deaza-guanosine and 7-deaza-adenosine into the amplified DNA since these compounds are reported to stabilize the nucleic acid during mass spectrometry (Schneider and Chait, 1995).

EXAMPLE II

Mass Spectrometry of a Nucleic Acid Sample

Advances in the art of mass spectrometry over about the last eight years have enabled mass spectrometry to be applied to biopolymers including nucleic acids (for an early review see Hillenkamp et al., 1991). One breakthrough was the use of a matrix to embed the sample to be tested. This technique is referred to as matrix-assisted laser desorption/ionization mass spectrometry (MALDI-MS). Several different matrices have been developed which yield good results with biopolymers. One of the more useful matrices is 3-hydroxypicolinic acid. Some other matrices which have been used with polynucleotides are a mixture of anthranilic acid and nicotinic acid, succinic acid, 2,4,6-trihydroxy acetophenone, 2,5-dihydroxybenzoic acid, etc (Hillenkamp et al., 1991; Bing and Biemann, 1994). An ion source is needed to desorb the sample. Pulsed lasers are used for this purpose. The type of laser used produces specific wavelengths and these must be appropriate for the matrix which is being used. A preferred combination for polynucleotides is to use a neodymium-garnet solid state laser in combination with a 3-hydroxypicolinic acid matrix.

EXAMPLE III

Amplification and Analysis of a Gene Fragment To Determine the Possible Presence of an Insertion Known to be Associated with a Disease A patient is to be tested for the possible presence of a mutation in a gene which can cause breast cancer if it is mutated. Much data is presently available for such a gene, BRCA1, and several mutations in this gene associated with breast cancer have been discovered. The cDNA for BRCA1 has been completely sequenced and the locations of several mutations which cause breast cancer have been determined (Miki et al., 1994; Futreal et al., 1994). This cDNA encodes a protein of 1863 amino acids and consists of 24 exons. Codon 1756 which is encoded by exon 20 in the wild-type gene has been found to contain an insertion of a C in some patients with breast cancer. The DNA sequence centered around this codon is as follows:

CAAAGCGAGCAAGAGAATCCCAGGACA-GAAAGATCTTCA (SEQ ID NO: 1).

Insertion of a C yields the following sequence:

CAAAGCGAGCAAGAGAATCCCCAGGACA-GAAAGATCTTCA (SEQ ID NO: 2). Because this region is known, primers may be made complementary to the 5' and 3' ends of this sequence and a polymerase chain reaction performed to amplify the region, yielding an amplified product of 39 or 40 base pairs. This amplified product is purified away from the primers by any suitable method well known to those in the art. The amplified fragment is denatured and the strands are separated. Techniques for purifying a single strand are known to those of skill in the art. One of the more commonly used techniques is to label one of the primers used for amplification with biotin. The biotin labeled strand is then captured by binding to streptavidin. The amplified single-stranded fragment is analyzed via mass spectrometry, e.g., via MALDI-MS using a 3-hydroxypicolinic acid matrix and a neodymium-garnet laser. The molecular weight for each phosphorylated deoxynucleotide is approximately as shown in Table I.

TABLE I

| pA | 329 |
| pC | 305 |
| pG | 345 |
| pT | 320 |

The insertion of a C in codon 1756 adds a G:C base pair to the amplified double-stranded fragment. This results in the amplified mutated fragment having a mass which is 305 Daltons more in the sense strand and 345 Daltons more in the antisense strand than the wild-type fragment. This difference of either 305 or 345 Daltons (depending on which strand is selected for analysis) is very readily detected from the mass spectrum obtained.

If a mutational insertion or deletion of an A:T base pair were to be observed, the difference in mass for a single strand would be approximately 329 or 320 Daltons. This would be just as easily seen as the insertion or deletion of a G:C base pair.

Insertions or deletions of more than a single base pair would also be easily identified.

EXAMPLE IV

Determination of a Transitional or Transversional Mutation

The method used in Example III is not useful for determining the presence of a polymorphism which is simply a result of a base change, i.e., a transition or a transversion. This is because regardless of the change, the wild-type DNA fragment and the mutated fragment will have nearly identical masses. A change of an A:T to a T:A will increase the mass of one strand by approximately 9 Daltons and decrease the mass of the complementary strand by approximately 9 Daltons. If a 40 base fragment were to be analyzed the total mass would be approximately 13,000 Daltons. A change of only 9 Daltons is likely to be undetectable. Assuming one wants to amplify the DNA using PCR, primers of at least 13 base pairs in length will be necessary. Therefore the shortest amplified fragment will consist of greater than 26 base pairs. Even at only a length of 30 bases (mass of about 9750 Daltons) it is unlikely that a change of only 9 Daltons will be observable. The present invention overcomes this problem by using any one of several techniques as detailed below.

A) Polymorphism Causes a Change in a Restriction Enzyme Site: Purifying a Single-stranded Fragment for Analysis A polymorphism may cause a change in a recognition sequence for a restriction endonuclease. An example can be given using a mutation in BRCA1 known to be associated with causing breast cancer. A G to T transversion in codon 1541 changes a GAG codon which encodes glutamic acid to a TAG stop codon. The DNA sequence in the immediate region of codon 1541 in the wild-type is:

TGGAGGAGCAACAGCTGGAA-GAGTCTGGGCCACACGATTT (SEQ ID NO: 3). Codon 1541 is shown in underlined bold-faced type. The mutation changes the first G of the codon to a T. The restriction enzyme Mbo II recognizes the sequence

5' . . . GAAGA($N_8$)↓ . . . 3'

3' . . . CTTCT($N_7$)↑ . . . 5'

This restriction site is present just at the site of the mutation. The wild-type sequence contains the restriction site but the mutated sequence will not be recognized by the enzyme. By amplifying this DNA fragment (using a biotin labeled primer for the sense strand), digesting with Mbo II, and purifying the sense strand, wild-type DNA will yield a strand of 30 bases in length (Mbo II cutting 8 bases 3' of the last A of the recognition site). The mutated version will not be recognized by Mbo II and a complete length strand of 40 bases will be seen. The other fragments, e.g. the 10 base 3' fragment of wild-type, will not be present because it will not be labeled with biotin and will not be captured by the streptavidin capture step. The difference between fragments of 30 and 40 bases is easily detected via MALDI-MS.

B) Polymorphism Causes a Change in a Restriction Enzyme Site: Denaturation and Analysis of Both Strands One need not purify the single strands of DNA as in Example IV-A. An alternative is simply to amplify the 40 base pair fragment, digest with Mbo II, purify the DNA, then denature the purified DNA and analyze it via mass spectrometry. In mutated DNA with no recognition sequence, the two single strands will each be 40 bases in length. The sense strand will consist of 7 Ts, 14 Gs, 1 As and 8 Cs and have a mass of approximately 13,129 Daltons. The antisense strand will consist of 11 Ts, 8 Gs, 7 As and 14 Cs and have a mass of approximately 12,853 Daltons. The mass spectrum will show two major peaks in the region of the corresponding masses. Other minor peaks may occur due to multiply charged species or degradation products. These will help create a "signature" spectrum for the mutated fragment. The wild-type fragment will yield a completely different spectrum. The 40 base pair double stranded fragment will be digested by Mbo II and upon denaturation there will be 4 single-stranded fragments present. These will consist of 30 base and 10 base fragments resulting from the sense strand and 29 base and 11 base fragments resulting from the antisense strand. The masses of these four fragments are approximately 9922, 3207, 9196 and 3632 Daltons, respectively. Again there will likely be minor bands appearing due to multiply charged fragments and degradation products. There may also be larger bands resulting from incomplete digestion with Mbo II. The signature spectrum of the wild-type digested DNA will obviously be quite different from that of the mutated DNA. The major peaks which will be seen in the spectrum from amplifying the 40 base pair fragment, digesting with Mbo II and then analyzing via MALDI-MS are as shown in Table II.

TABLE II

| Masses of the Major Peaks Observed | |
| --- | --- |
| Wild-type | Mutated |
| 3207 | 12828 |
| 3632 | 13104 |
| 9196 | |
| 9922 | |

This last technique is very simple and will likely have wide although probably not universal applicability. Because one is screening DNA in regions of known mutations, the sequences are already known and it is simple to determine proper primers for PCR. There is a very large number of known restriction enzymes with different recognition sequences to choose from and there is a reasonable chance of finding one which will recognize the wild-type but not the mutated DNA or vice versa. Again, because one is dealing with known sequences it is simply a matter of looking through a catalog of available restriction enzymes to find an appropriate one.

If desired, this last method can be modified. Larger fragments of DNA may be generated via PCR or other amplification method. This may be necessary if no suitable primers can be designed to give a smaller fragment. It may also be done to examine more than one mutation at a time if two or more mutations are relatively close to each other. These long fragments are then digested with a series of restriction enzymes to produce a mix of several sizes of DNA fragments. This complete mix is then analyzed via mass spectrometry. The resulting signature spectrum will consist of several major peaks. As an example, assume an initial fragment of 1,500 base pairs was synthesized via PCR and digested with a mix of restriction enzymes, e.g., Bam HI, Eco RI and Hind III. The digestion products in this hypothetical are 20 fragments of sizes shown in Table III arranged by size, not by location along the fragment.

TABLE III

| Fragment No. | Size in Base Pairs |
| --- | --- |
| 1 | 20 |
| 2 | 24 |
| 3 | 25 |
| 4 | 30 |
| 5 | 32 |
| 6 | 35 |
| 7 | 35 |
| 8 | 40 |
| 9 | 50 |
| 10 | 55 |

TABLE III-continued

| Fragment No. | Size in Base Pairs |
| --- | --- |
| 11 | 65 |
| 12 | 66 |
| 13 | 68 |
| 14 | 70 |
| 15 | 85 |
| 16 | 100 |
| 17 | 120 |
| 18 | 140 |
| 19 | 180 |
| 20 | 260 |

Further, for this hypothetical example assume that there is one mutation known to occur in fragment I and one mutation known to occur in fragment 6. One mutation affects a Hind III site and the other affects a Bam HI site present in the wild-type. Analyzing this complete mix will give one spectrum (as shown in Table III) for wild-type DNA. A different spectrum will be seen if one or both of the mutations are present. If the mutation affecting fragment 1 is present the 20 base fragment will no longer appear. If the mutation affecting fragment 6 is present, the peak at a size representing 35 nucleotides will be one half of its initial height. (Note that this assumes that the two 35 base single stranded fragments (fragments 6 and 7) are of equal mass. If they are of unequal mass then one of the peaks will disappear.) One other peak will also disappear with the occurrence of each mutation. If the mutation affecting fragment 1 also affects fragment 10 (the Hind III site is at the junction of fragments 1 and 10) then the 55 base peak will also disappear and a new peak corresponding to the sum of fragments 1 and 10 (20+55=75 base pairs) will appear. It will be irrelevant whether the large fragments of DNA can be properly analyzed because the enzymes are chosen to produce short fragments which will be affected by the mutations.

EXAMPLE V

Completely Digesting an Amplified DNA Fragment with DNAse

Another variation for determining the presence of a polymorphism using a mass spectrometry analysis is to amplify the DNA of interest and then totally digest it with an exonuclease such as deoxyribonuclease II (DNAse II). This enzyme completely cleaves polynucleotides to mononucleotides. Using this method to analyze the mutation occurring at codon 1541 of BRCA1 (see Example IV-A above) gives the following results:

A) Analyzing the 40 base pair double-stranded fragment

If both strands are present, digestion with DNAse II will result in the presence of 18 Ts, 22 Gs, 18 As and 22 Cs in the wild-type DNA. When the mutation is present the breakdown is 19 Ts, 21 Gs, 19 As and 21 Cs. Four major peaks will be seen, one for each nucleotide. These will be at approximately masses of 320 (Tp), 345 (Gp), 329 (Ap), and 305 (Cp). The relative peak heights or intensities will change depending on the composition of the DNA. When mutated DNA is analyzed for this example, the peak heights for T and A will be larger while the peak heights for G and C will be smaller as compared with wild-type DNA. In this example the change in peak height is approximately 5% for each of the peaks. Use of fragments shorter than 40 base pairs will usually yield a greater relative change in peak intensity.

This method is also applicable to analyzing for insertions or deletions. Again a difference in peak height will be seen when wild-type and mutant spectra are compared. For the BRCA1 mutation discussed in Example III, there would be an addition of 1 extra C and 1 extra G thereby increasing those two peaks and having no effect on the A and T peaks.

B) Analyzing Only a Single-Stranded DNA

The method used in part A above can be modified to yield a more sensitive technique. As always, amplified DNA is prepared. For this example use one primer labeled with biotin and then purify the single strand - here the sense strand of the BRCA1 fragment containing codon 1541. This single strand of 40 bases (with the 5' T being biotinylated) is digested with deoxyribonuclease I (DNAse I) which is an enzyme which will cleave single-stranded DNA preferentially next to pyrimidines to yield 5'-phosphate terminated polynucleotides with 3'-OH termin. In the case of the 40 base fragment from BRCA1, the fragments which will result from wild-type DNA are shown in Table IV.

TABLE IV

| Fragment | Wild Type Sequence | Mass | Mutated Sequence | Mass |
|---|---|---|---|---|
| 1 | T(biotinylated) | 563 | T(biotinylated) | 563 |
| 2 | GGAGGAGC | 2688 | GGAGGAGC | 2688 |
| 3 | AAC | 963 | AAC | 963 |
| 4 | AGC | 979 | AGC | 979 |
| 5 | T | 320 | T | 320 |
| 6 | GGAAGAGT | 2687 | GGAAT | 1668 |
| 7 | C | 305 | AGT | 994 |
| 8 | T | 320 | C | 305 |
| 9 | GGGC | 1340 | T | 320 |
| 10 | C | 305 | GGGC | 1340 |
| 11 | AC | 634 | C | 305 |
| 12 | AC | 634 | AC | 634 |
| 13 | GAT | 994 | AC | 634 |
| 14 | T | 320 | GAT | 994 |
| 15 | T | 320 | T | 320 |
| 16 | — | — | T | 320 |

Rearranging this data by mass and number of fragments of the particular mass yields Table V.

TABLE V

| Mass | Number of Fragments Wild-type | Mutated |
|---|---|---|
| 305 | 2 | 2 |
| 320 | 4 | 4 |
| 563 | 1 | 1 |
| 634 | 2 | 2 |
| 963 | 1 | 1 |
| 979 | 1 | 1 |
| 994 | 1 | 2 |
| 1340 | 1 | 1 |
| 1668 | — | 1 |
| 2687 | 1 | — |
| 2688 | 1 | 1 |

Analysis of this data reveals differences between the two spectra at masses of 994, 1668 and 2687. The peak at 994 is twice as large in the mutated sample as in the wild-type, the peak at 1668 is present only for the mutated sample, and the peak at 2687 is present only in the wild-type. The "signature" of each spectrum is distinctive and clearly different from the other spectrum.

EXAMPLE VI

Analysis of Ribonucleic Acid

Analysis for the presence of polymorphisms using mass spectrometry need not be limited to using DNA. RNA is just as suitable and has actually been reported to be more stable and less prone to degradation during mass spectrometry. Those of skill in the art will know a number of ways in which to prepare RNA fragments for the region of interest to be analyzed. Amplified fragments of DNA may be cloned into vectors which contain RNA polymerase promoters. These vectors are linearized at the end of the insert away from the promoter and RNA transcripts can be produced in large quantities. This yields a single-stranded RNA which can be assayed essentially in the same manner as single-stranded DNA as discussed above. It is also possible to "transcribe" an amplified DNA fragment to produce RNA. Since genes of known sequence are to be analyzed, the sequence is already known (except for the possibility of a mutation or polymorphism in the region to be tested) and it is a simple matter to design an appropriate primer. For assays involving digesting the RNA with nucleases, rather than restriction enzymes or DNAses one will of course use RNAses. These may be used singly or in combinations. Some ribonucleases which are available commercially are ribonuclease A (hydrolyzes the 3' side of pyrimidines), ribonuclease $T_1$ (hydrolyzes the 3' side of G), ribonuclease $T_2$ (hydrolyzes the 3' side of purines and at pyrimidines), and ribonuclease $U_2$ (cleaves the 3' side of purines).

EXAMPLE VII

Analysis of cDNA

Complementary DNA (cDNA) may be analyzed exactly as genomic DNA was analyzed above. In the examples above, mutations occurred in the middle of exons and genomic DNA was amplified by PCR using primers complementary to the exon around the region of the mutation. One may also prepare cDNA to accomplish this same purpose. Preparation of cDNA is well known to those of skill in the art. Briefly, one purifies messenger RNA (mRNA), reverse transcribes this mRNA to produce an RNA:DNA hybrid, hydrolyzes the mRNA to leave a single-stranded DNA, and finally synthesizes the complementary strand to form a double stranded DNA. This cDNA is a mixture of all of the expressed genes. The cDNA may then be specifically amplified via PCR or some other amplification technique. The use of cDNA limits one to analyzing mutations which occur in exons. To analyze for a polymorphism which occurs in an intron it is necessary to analyze genomic DNA.

The above examples are clearly not all encompassing. Many variations will be readily apparent to those skilled in the art. Amplification need not be performed by PCR but can be done by any other suitable amplification technique. Digestion of samples may be done in a variety of ways— either using enzymes other than those specified in the examples or simply by chemical cleavage of the polynucleotides. Purification of single strands can also be accomplished by a number of techniques known to those skilled in the art. Use of biotin and streptavidin is only one such technique. Also, as noted earlier, a large variety of nucleotide analogs may be used. These will have different purposes. Increased stability of nucleic acids has been reported for those containing 7-deaza-guanosine and 7-deaza-adenosine. Incorporation of deoxyuridine into the amplified DNA allows one to remove these bases using uracil-N-glycosidase digestion. The matrix used for the mass spectrometry need not be limited to 3-hydroxy-picolinic acid. Other matrices are also suitable, although many researchers have found 3-hydroxy-picolinic acid to be most suitable for polynucleotide analysis. The choice of exactly what type of mass spectrometer or laser source is also a variable. Again, MALDI-MS using a neodymium-garnet laser is a favored choice.

The invention as described above enhances the rapidity of analysis for polymorphisms in known genes. The method does not require DNA sequencing or hybridization techniques and therefore does away with the need for running gels or hybridizing samples. The nucleic acid is prepared, amplified and purified, possibly digested, and then analyzed via mass spectrometry. Differences in the signature of the spectrum obtained as compared to known signature spectra make the presence or absence of a polymorphism readily apparent. The throughput of samples in the mass spectrometer is estimated to be 1–2 seconds with analysis occurring off-line. The BRCA1 gene encodes 1863 amino acids corresponding to 5589 base pairs. Many different mutations associated with breast cancer have now been found in this gene. It will require analysis of many different fragments if one is concerned with analyzing the complete gene. (If a relative has a known mutation one may simply wish to analyze for that single mutation.) Mass spectrometers are presently available which have target slides with 64 sample spots that can be deposited by robot. Using a 100 Hz laser for 1 second of collection time (about 50 samplings) and 1 second for slide movement requires 128 seconds for the 64 samples. Thus one can analyze for at least 64 distinct mutations in about 2 minutes of mass spectrometry time. The sample preparation time is not included here, but sample preparation is just as time consuming in other techniques such as DNA sequencing. The off-line analysis is quite simple and quick, a comparison of the spectra with known signature spectra for either the wild-type sequence or for a sequence with a known polymorphism.

The utility of the method need not be limited to analyzing for mutations or polymorphisms in known genes associated with diseases. It may be used to screen candidate gene sequences for mutations in a positional cloning project. It may also be used for other types of comparative DNA analyses such as genotyping.

LIST OF REFERENCES

P. A. Futreal, Q. Liu, D. Shattuck-Eidens, C. Cochran, K. Harshman, S. Tavtigian, L. M. Bennett, A. Haugen-Strano, J. Swensen, J. Weaver-Feldhaus, W. Ding, Z. Gholami, P. Soderkvist, L. Terry, S. Jhanwar, A. Berchuck, J. D. Iglehart, J. Marks, D. G. Ballinger, J. C. Barrett, M. H. Skolnick, A. Kamb and R. Wiseman (1994). *Science* 266:120–122.

F. Hillenkamp, M. Karas, R. C. Beavis and B. T. Chait (1991). "Matrix-Assisted Laser Desorption/Ionization Mass Spectrometry of Biopolymers", *Anal. Chem.* 63:1193A–1203A.

F. Kirpekar, E. Nordhoff, K. Kristiansen, P. Roepstorff, A. Lezius, S. Hahner, M. Karas and F. Hillenkamp (1994). "Matrix assisted laser desorption/ionization mass spectrometry of enzymatically synthesized RNA up to 150 kDa", *Nucl. Acids Res.* 22:3866–3870.

A. M. Maxam and W. Gilbert (1977). *Proc. Natl. Acad. Sci. USA* 74:560.

Y. Miki, J. Swensen, D. Shattuck-Eidens, P. A. Futreal, K. Harshman, S. Tavtigian, Q. Liu, C. Cochran, L. M. Bennett, W. Ding, R. Bell, J. Rosenthal, C. Hussey, T. Tran, M. McClure, C. Frye, T. Hattier, R. Phelps, A. Haugen-Strano, H. Katcher, K. Yakumo, Z. Gholami, D. Shaffer, S. Stone, S. Bayer, C. Wray, R. Bogden, P. Dayananth, J. Ward, P. Tonin, S. Narod. P. K. Bristow, F. H. Norris. L. Helvering, P. Morrison, P. Rosteck, M. Lai, J. C. Barrett, C. Lewis, S. Neuhausen, L. Cannon-Albright, D. Goldgar, R. Wiseman, A. Kamb, M. H. Skolnick (1994). *Science* 266:66–71.

R. W. Nelson, M. J. Rainbow, D. E. Lohr, and P. Williams (1989). "Volatilization of High Molecular Weight DNA by Pulsed Laser Ablation of Frozen Aqueous Solutions", *Science* 246:1585–1587.

E. Nordhoff, R. Cramer, M. Karas, F. Hillenkamp, F. Kirpekar, K. Kristiansen and P. Roepstorff (1993). "Ion stability of nucleic acids in infrared matrix-assisted laser desorption/ionization mass spectrometry", *Nucl. Acids Res.* 21:3347–3357.

E. Nordhoff, F. Kirpekar, M. Karas, R. Cramer, S. Hahner, F. Hillenkamp, K. Kristiansen, P. Roepstorff and A. Lezius (1994). "Comparison of IR- and UV-matrix-assisted laser desorption/ionization mass spectrometry of oligodeoxynucleotides", *Nucl. Acids Res.* 22:2460–2465.

U. Pieles, W. Zurcher, M. Schar and H. E. Moser (1993). "Matrix-assisted laser desorption ionization time-of-flight mass spectrometry: a powerful tool for the mass and sequence analysis of natural and modified oligonucleotides", *Nucl. Acids Res.* 21:3191–3196.

F. Sanger, S. Nicklen and A. R. Coulson (1977). *Proc. Natl. Acad. Sci. USA* 74:5463.

K. Schneider and B. T. Chait (1995). "Increased stability of nucleic acids containing 7-deaza-guanosine and 7-deaza-adenosine may enable rapid DNA sequencing by matrix-assisted laser desorption mass spectrometry", *Nucl. Acids Res.* 23:1570–1575.

G. Siuzdak (1994). "The emergence of mass spectrometry in biochemical research", *Proc. Natl. Acad. Sci. USA* 91:11290–11297.

B. H. Wang and K. Biemann (1994). "Matrix-Assisted Laser Desorption/Ionization Time-of-Flight Mass Spectrometry of Chemically Modified Oligonucleotides", *Anal. Chem.* 66:1918–1924.

K. J. Wu, T. A. Shaler and C. H. Becker (1994). "Time-of-Flight Mass Spectrometry of Underivatized Single-Stranded DNA Oligomers by Matrix-Assisted Laser Desorption", *Anal. Chem.* 66:1637–1645.

What is claimed is:

1. A method to analyze for a polymorphism or a mutation in a gene or a portion of said gene encoded by a nucleic acid by a) denaturing said nucleic acid or a portion of said nucleic acid to produce a denatured nucleic acid, b) performing mass spectrometry on said denatured nucleic acid to obtain a mass spectrum, c) comparing the obtained mass spectrum with reference mass spectra obtained of the nucleic acid in its wild-type, polymorphic, or mutated state, and d) determining whether the obtained mass spectrum matches a reference spectrum for either the wild-type nucleic acid or the nucleic acid having said polymorphism or mutation, wherein a match with said wild-type nucleic acid indicates that said gene is wild-type and a match with said nucleic acid having said polymorphism or mutation indicates that said gene has said polymorphism or mutation, a match being indicated by identity of peak locations (representing mass) and relative peak heights (representing quantity), with the proviso that said method does not comprise sequencing said nucleic acid.

2. The method according to claim 1 wherein a portion of said nucleic acid is analyzed.

3. A method to analyze for a polymorphism or a mutation in a portion of a gene encoded by a nucleic acid by a) denaturing said nucleic acid encoding said portion of said gene to produce a denatured nucleic acid, b) amplifying said denatured nucleic acid to produce an amplified nucleic acid, c) performing mass spectrometry on said amplified nucleic acid to obtain a mass spectrum, d) comparing the obtained mass aspect with reference mass spectra obtained of the nucleic acid in its wild-type, polymorphic, or mutated state, and e) determining whether the obtained mass spectrum matches a reference spectrum for either the wild-type nucleic acid or the nucleic acid having said polymorphism or mutation, wherein a match with said wild-type nucleic acid indicates that said gene is wild-type and a match with said nucleic acid having said polymorphism or mutation indicates that said gene has said polymorphism or mutation, a match being indicated by identity of peak locations (representing mass) and relative peak heights (representing quantity), with the proviso that said method does not comprise sequencing said nucleic acid.

4. The method according to claim 3 wherein said amplified nucleic acid is digested prior to denaturation and analysis.

5. The method according to claim 4 wherein digestion is performed using one or more restriction endonucleases.

6. The method according to claim 4 wherein digestion is performed using a deoxyribonuclease.

7. The method according to claim 4 wherein digestion is performed using chemical cleavage.

8. The method according to claim 4 wherein following digestion the digested nucleic acid is denatured and a single-stranded nucleic acid fragment is purified and analyzed.

9. The method according to claim 5 wherein following digestion the digested nucleic acid is denatured and a single-stranded nucleic acid fragment is purified and analyzed.

10. The method according to claim 3 wherein the amplified nucleic acid is denatured and a single-stranded nucleic acid fragment is purified and analyzed.

11. The method according to claim 3 wherein said amplification produces an RNA fragment.

12. A method to analyze for a polymorphism or mutation in a portion of a gene encoded by a nucleic acid by a) cloning said nucleic acid into a vector containing one or more RNA promoters, b) synthesizing RNA using said vector with said nucleic acid as a template, c) performing mass spectrometry on said RNA to obtain a mass spectrum, d) comparing the obtained mass spectrum with reference mass spectra obtained of the RNA in its wild-type, polymorphic, or mutated state, and e) determining whether the obtained mass spectrum matches a reference spectrum for either the wild-type RNA or the RNA having said polymorphism or mutation, wherein a match with the wild-type RNA indicates that said gene is wild-type and a match with said RNA having said polymorphism or mutation indicates that said gene has said polymorphism or mutation, a match being indicated by identity of peak locations (representing mass) and relative peak heights (representing quantity), with the proviso that said method does not comprise sequencing said RNA.

* * * * *